(12) United States Patent
Li

(10) Patent No.: US 9,375,226 B2
(45) Date of Patent: Jun. 28, 2016

(54) SURGICAL INSTRUMENT

(75) Inventor: Jiangming Li, Shijiazhuang (CN)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 180 days.

(21) Appl. No.: 12/727,935

(22) Filed: Mar. 19, 2010

(65) Prior Publication Data

US 2011/0230725 A1 Sep. 22, 2011

(51) Int. Cl.
*A61B 1/32* (2006.01)
*A61B 17/28* (2006.01)
*A61B 17/24* (2006.01)

(52) U.S. Cl.
CPC ............... *A61B 17/282* (2013.01); *A61B 17/24* (2013.01); *A61B 2017/2808* (2013.01)

(58) Field of Classification Search
USPC .......... 600/208–210, 218; 606/151, 157–158, 606/205–209, 185, 188; 81/418–420, 81/424.5, 426, 426.5; 433/157, 159
See application file for complete search history.

(56) References Cited

U.S. PATENT DOCUMENTS

| | | | | | |
|---|---|---|---|---|---|
| 1,985,108 | A | * | 12/1934 | Rush | A61B 17/8866 606/86 R |
| 2,187,929 | A | * | 1/1940 | Blanc | 269/48.2 |
| 2,798,491 | A | * | 7/1957 | Samuels | 606/188 |
| 3,364,933 | A | * | 1/1968 | Leopold | A61B 17/282 606/207 |
| 3,786,815 | A | * | 1/1974 | Ericson | 606/207 |
| 4,120,302 | A | * | 10/1978 | Ziegler | 606/207 |
| 4,300,564 | A | * | 11/1981 | Furihata | 606/127 |
| 4,611,592 | A | * | 9/1986 | Talboy | 606/207 |
| 4,803,983 | A | * | 2/1989 | Siegel | 606/151 |
| D307,322 | S | * | 4/1990 | Dolwick | D24/135 |
| 5,058,414 | A | * | 10/1991 | Hayes | 72/379.2 |
| 5,447,515 | A | * | 9/1995 | Robicsek | 606/158 |
| 5,891,162 | A | * | 4/1999 | Sugarbaker et al. | 606/207 |
| 5,944,723 | A | * | 8/1999 | Colleran et al. | 606/88 |
| 6,261,296 | B1 | * | 7/2001 | Aebi | A61B 17/025 600/219 |
| 6,293,790 | B1 | * | 9/2001 | Hilliard | 433/4 |
| 7,264,623 | B2 | * | 9/2007 | Harris et al. | 606/148 |
| 8,876,905 | B2 | * | 11/2014 | Frasier | A61F 2/44 623/17.11 |
| 2004/0092979 | A1 | * | 5/2004 | Burbank et al. | 606/158 |
| 2004/0153105 | A1 | * | 8/2004 | Burbank et al. | 606/157 |
| 2005/0131432 | A1 | * | 6/2005 | Gold et al. | 606/153 |
| 2007/0219582 | A1 | * | 9/2007 | Brunelle et al. | 606/207 |

* cited by examiner

*Primary Examiner* — Jan Christopher Merene
*Assistant Examiner* — Steven Cotroneo
(74) *Attorney, Agent, or Firm* — Maschoff Brennan

(57) ABSTRACT

The present disclosure relates to a surgical instrument having a first elongated member and a second elongated member and a connector pivotably interconnecting the first elongated member and the second elongated member, where the first elongated member includes a partially or completely circumscribed opening, and the second elongated member includes a partially or completely circumscribed opening, or a support configured to correspond to the partially or completely circumscribed opening of the first elongated member that when operated between an open or closed state, engages or disengages an object to fix, confine and/or extrude the object with or through the partially or completely circumscribed opening of the first elongated member.

14 Claims, 6 Drawing Sheets

SURGICAL INSTRUMENT

TECHNICAL FIELD

The present disclosure is in the field of medical devices and surgical methods.

BACKGROUND

After the application of local anesthesia, due to tissue edema, it is difficult to find tumors of good mobility in the depths of a surgical field. During surgical operations in a small surgical field, such as in genal regions, surgeons often have to use their fingers to achieve compression hemostasis, which hampers suturing and may prolong the procedure and increase bleeding. In oral surgeries, the mucus coating inside the oral cavity further adds to the difficulty of tissue retraction and fixation.

SUMMARY

One aspect of the present disclosure provides a surgical instrument, comprising a first elongated member and a second elongated member each comprising an engaging end and a handle end connected by an elongated portion; and a connector located between the engaging end and the handle end of each elongated member, the connector interconnecting the first elongated member and the second elongated member such that the first elongated member and the second elongated member are configured to pivot around the connector, wherein the engaging end of the first elongated member includes an at least partially circumscribed opening, and the engaging end of the second elongated member includes a support configured to at least partially correspond to the at least partially circumscribed opening.

Another aspect of the present disclosure also provides a surgical instrument, comprising: a first elongated member and a second elongated member each having an engaging end and a handle end that are connected by an elongated portion; and a connector interconnecting the first elongated member and the second elongated member such that the first elongated member and the second elongated member are configured to pivot around the connector. The engaging end of the first elongated member includes a partially circumscribed opening, and the engaging end of the second elongated member includes an at least partially circumscribed opening.

The present disclosure also provides a method of operating a surgical instrument, the method comprising: operating a handle of a surgical instrument to place a partially or completely circumscribed opening of an engaging end of a first elongated member and a partially or completely circumscribed opening or a support of an engaging end of a second elongated member away from each other in an open state or an unengaged state; and operating the handle of the surgical instrument to rotate the engaging ends relative to each other to place the engaging ends in a closed state or an engaged state, wherein a space at least partially enclosed by the circumscribed opening at least partially frames a section of a treatment site.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
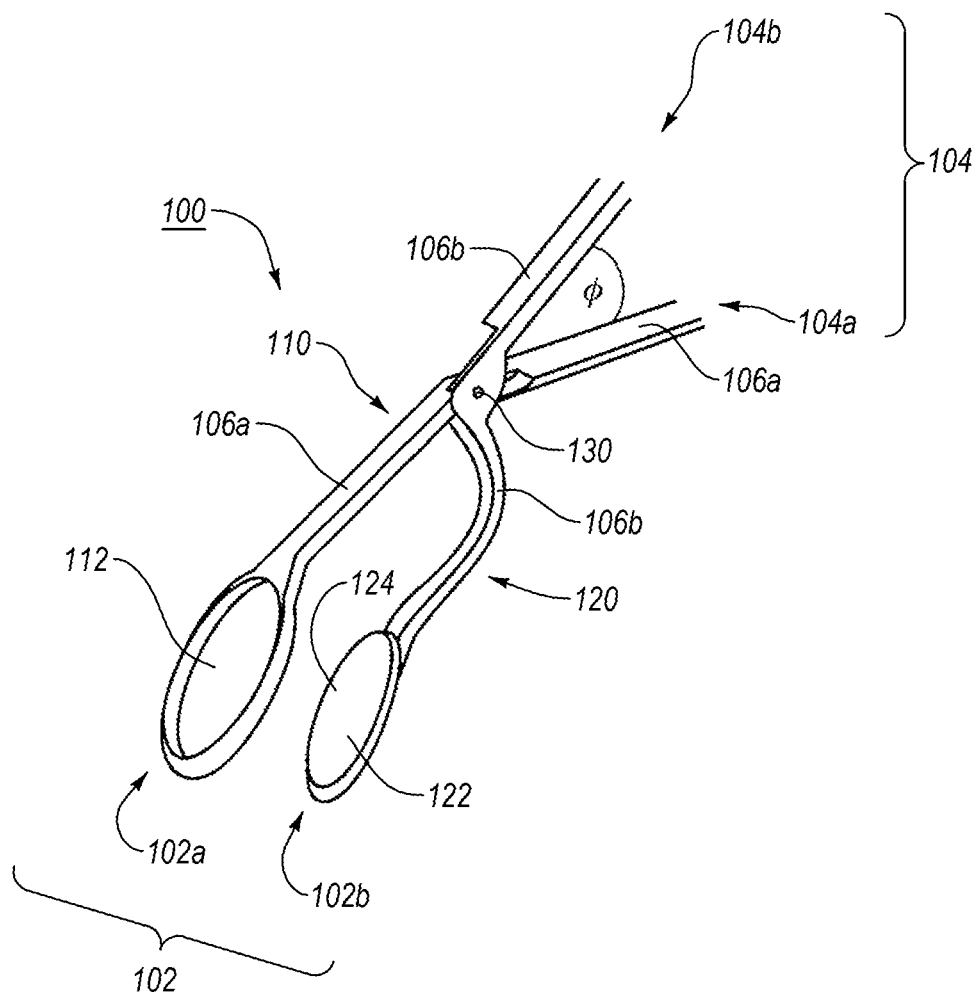
FIG. 1 shows a perspective view of part of an illustrative embodiment of a surgical instrument.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

During surgical procedures, it is sometimes difficult to confine a target site and/or to achieve compression hemostasis. For example, in a genal region, surgeons often have to use their fingers to grasp a particular area to be sutured, which can be difficult when the area is malleable, swollen, and/or coated with mucus, blood or other body fluids. This can lead to a prolonged surgical procedure, additional trauma to a surgical site, and/or increased bleeding.

Illustrative embodiments herein are generally directed to medical devices and surgical methods that enable a medical technician to retract and/or fixate a particular area so that it is easier to work with the particular area. As used herein, the term "medical technician" or simply "technician" will refer to any one who is tasked with using the instruments or performing the methods disclosed herein, including, but not limited to, a surgeon, a physician, a nurse, as well as a veterinarian, and any other medical assistants. The surgical instrument disclosed has a handle to be used by a technician to manipulate a working end. The working end is configured to be placed at the particular site of interest, for example, in a genal region of a subject's mouth. As used herein, the term "subject" should be broadly construed to include human subjects as well as animal subjects of all kinds, such as, but not limited to, domesticated animals, zoo animals, farm animals, wild animals, endangered animals, race animals, working animals, pets, and aquatic animals, among others. Illustrative examples of animals may include, but are not limited to, mammals such as canines (e.g., dogs), felines (e.g., cats), and equines (e.g., horses), birds, amphibians, reptiles, and other animal subjects. In some other embodiments, the area may be a section of a mucous membrane, a section of a mesentery, a section of muscle in/on a subject's body, a piece of skin for grafting, or an organ tissue for surgery/biopsy, among others. In one embodiment, the working end is configured to hold, alternatively or additionally, other objects such as, but not limited to, a sponge or bandage, a surgical tube, a piece of artificial tissue for grafting, a transplant organ, and the like.

In further detail, the surgical instrument has a first elongated member and a second elongated member each comprising an engaging end and a handle end connected by an elongated portion; and a connector located between the engaging end and the handle end of each elongated member, the connector interconnecting the first elongated member and the second elongated member such that the first elongated member and the second elongated member are configured to pivot around the connector. The engaging ends of the first and second elongated members thus operate together to form a working end of the surgical instrument. The handle ends of the first and second elongated members operate to form a handle of the surgical instrument.

The location of the connector may be anywhere along the elongated portions of the first and second elongated members. In some embodiments, the connector is located at an intermediate position along a length of the elongated portions of the first and second elongated members. In an illustrative embodiment, the connector is located at approximately the center of a length of one or both elongated portions of the first and second elongated members. In another illustrative embodiment, the connector is located eccentrically and the length between the connector and the handle ends exceeds that between the connector and the engaging ends of one or both elongated members. In still another illustrative embodiment, the connector is located eccentrically and the length between the connector and the handle ends is shorter than that between the connector and the engaging ends of one or both elongated members.

The connector may be any suitable connecting mechanism to allow the first elongated member and the second elongated member to pivot in relation to each other. In one embodiment, a pivot axis formed by the connector provides that both the elongated members can pivot around the connector. In one embodiment, the elongated members can rotate in an angle of about 0° to about 180°, about 2° to about 160°, about 5° to about 140°, about 10° to about 120°, or about 30° to about 90°, as illustrative examples. In one embodiment, a stop may be formed on one or both elongated members to limit the angle of rotation that one or both elongated members can pivot. In an illustrative embodiment, the connector may be an axis passing through holes in the first and second elongated member. Alternatively or additionally, the connector can be a screw joint, a box joint, a stub joint, a rivet, or the like.

In one embodiment, the engaging ends of the first and second elongated members are configured to operably cooperate with each other to hold an object therebetween. That is, the object can be firmly held by the engaging ends of the first and second elongated members, similar to the operation of a surgical clamp. The amount of firmness with which the engaging ends of the first elongated member and the second elongated member hold an object can range from a tight hold on the object by the engaging ends of the first elongated member and the second elongated member to a lighter hold on the object in which the engaging ends of the first elongated member and the second elongated member are barely touching the object. In some embodiments, the amount of firmness with which the engaging ends of the first elongated member and the second elongated member hold an object is sufficient to achieve compression hemostasis in the surrounding tissue, as with a hemostat, which may be desirable in some surgical procedures. As discussed above, the types of objects that can be held by the engaging ends of the first elongated member and the second elongated member are numerous and varied. Objects may include portions of a subject's body such as, but not limited to, a section of a mucous membrane, a section of a mesentery, a section of muscle in/on a subject's body, a piece of skin for grafting, or an organ tissue for surgery/biopsy, among others. Objects can also include other medical devices used for performing a medical procedure including, but not limited to, a sponge or bandage, a surgical tube, a piece of artificial tissue for grafting, a transplant organ, and the like.

As described below, a technician manipulates the handle, and, due to the pivotable connection formed by the connector in the first elongated member and second elongated member, moves the working end between an unengaged state and an engaged state to hold an object. Further, the technician manipulates the handle to move the working end from an engaged state to an unengaged state to release the object. When the engaging ends of the first and the second elongated members are holding the object, they are considered to be engaged with each other. As used herein, the term "engaged" or its variants, is to be construed broadly. In some embodiments, the engaging ends are engaged when they are brought into close proximity with each other to hold an object therebetween. So, in some embodiments, for smaller and/or thinner objects, the engaging ends may be "engaged" when they are about 0 mm to about 10 mm apart, about 1 mm apart to about 9 mm apart, or about 2 mm apart to about 8 mm apart, as illustrative examples. In one embodiment, the object may be thin enough that the engaging end of the second elongated member may pass through an at least partially circumscribed opening of the engaging end of the first elongated member, pushing a portion of the object through the at least partially circumscribed opening, as detailed below. In another embodiment, where the engaging ends are holding a larger object, the engaging ends may be engaged when they are about 10 mm apart to about 50 mm apart or even farther apart. For example, if the surgical instrument is configured for a larger surgical site, the engaging ends may be about 5 cm to about 20 cm apart, while holding an object to thereby become engaged.

In another embodiment, a technician manipulates the handle, and, due to the pivotable connection formed by the connector in the first elongated member and second elongated member, moves the working end between an open state and a closed state without requiring an object be held at the working end. In the closed state, the engaging ends of the first elongated member and the second elongated member are brought in close proximity with each other without holding an object. In some embodiments of this situation, the edges and/or surface of the engaging ends of the first elongated member and the second elongated member may come in contact with each other. In some other embodiments of the closed state, the engaging ends of the first elongated member and the second elongated member may be configured not to come in contact with each other, yet still be in close proximity with each other. In one such embodiment, the engaging end of the second elongated member is of a smaller size than an at least partially circumscribed opening formed on the engaging end of the first elongated member and may pass through the at least partially circumscribed opening without touching its edge. In the closed state, the engaging ends of the first elongated member and the second elongated member may be about 0 mm to about 10 mm apart, about 1 mm apart to about 9 mm apart, or about 2 mm apart to about 8 mm apart, as illustrative examples.

The engaging end of the first elongated member can have various configurations. In one embodiment, the engaging end of the first elongated member includes a partially circumscribed opening. In another embodiment, the engaging end of the first elongated member includes a completely circumscribed opening. As used herein, the term "circumscribed opening" used by itself will be understood to refer to both "partially circumscribed opening" and "completely circumscribed opening" embodiments. Further, the term an "at least partially circumscribed opening" will be understood to refer to both "partially circumscribed opening" and "completely circumscribed opening" embodiments. By providing partially and completely circumscribed opening options, additional flexibility is provided in the manner and type of locations in which the surgical instrument can be used. Because the rims of the partially circumscribed opening have ends that do not meet, a gap forms between the ends of the rims that provides a different opening configuration than for a completely circumscribed opening. Thus, the partially circumscribed opening may be able to fit in a surgical area in which a completely circumscribed opening is not able to fit due to the gap formed between the ends of the rims of the partially circumscribed opening. In another embodiment, a partially circumscribed opening may provide more accessible area of an object due to the gap formed between the ends of the rims of the partially circumscribed opening. This may allow more area of an object to be accessible through the partially circumscribed opening than a completely circumscribed opening because the area underneath the gap is not blocked. When the engaging end of the second elongated member pushes a portion of the object through the partially circumscribed opening, more area of an object can pass through the gap. Alternatively or additionally, a partially circumscribed opening may provide a different ability to hold an object using the surgical instrument. For example, when an object is passed through a partially circumscribed opening, more of the object may be available to the technician for surgical use than for a completely circumscribed opening, since the object is not blocked in the area of the gap.

The partially or completely circumscribed opening can be in the shape of, for example, an ellipse, a circle, a square, and a triangle with round corner contour. While these standard shapes are provided as examples, the partially or completely circumscribed opening can be in an irregular shape to fit a particular site or purpose such as irregular formations in skin, tissue, muscle, and the like. The length or diameter of the partially or completely circumscribed opening can be in the range of about 1 cm to about 50 cm, about 2 cm to about 40 cm, about 3 cm to about 30 cm, about 5 cm to about 15 cm, about 1 cm to about 10 cm, about 1 cm to about 6 cm, or about 2 cm to about 5 cm, e.g. approximately 2 cm, 3 cm, 4 cm, 5 cm, 6 cm, 10 cm, or 15 cm, as illustrative examples.

The size of the partially or completely circumscribed opening may depend on where (e.g. the subject and/or the location) and/or how the surgical instrument will be used. For examples, an operation in a person's or animal's genal region could require a smaller size of partially or completely circumscribed opening than an operation on a person's or animal's leg muscle. Furthermore, particular characteristics of the location will also contribute to the size of the partially or completely circumscribed opening. For example, a size of the partially or completely circumscribed opening may be based on a size of a tumor located on a particular site, or a size of a foreign body, e.g. a bullet, located on a particular site, and the like. Furthermore, a size of the partially or completely circumscribed opening may depend on the type of subject on which the surgical instrument is being used. For example, the genal region of a horse may be quite a bit larger than the genal region of a human.

The rim(s) of the partially or completely circumscribed opening may have a substantially circular cross-sectional shape, a substantially non-circular cross-sectional shape, or any combination thereof. Illustrative examples of non-circular cross-sectional shapes may include, but are not limited to, polygonal cross-sectional shapes, such as, but not limited to, rectangles, squares, hexagons, or trapezoids, to name a few, and cross-sectional shapes that include combinations of curved and straight lines. The cross-sectional thickness of the rim(s) may be proportionately sized for the circumscribed opening and may be in a range of about 1 mm to about 2 cm, about 1 mm to about 1 cm, or about 2 mm to about 5 mm, as illustrative examples. In some embodiments, the rim may be hollow and the weight of the instrument may be reduced to some extent.

Likewise, the engaging end of the second elongated member can have various configurations. In one embodiment, the engaging end of the second elongated member includes a partially circumscribed opening configured to at least partially correspond to the at least partially circumscribed opening of the engaging end of the first elongated member. In another embodiment, the engaging end of the second elongated member includes a completely circumscribed opening configured to at least partially correspond to the at least partially circumscribed opening of the engaging end of the first elongated member. When the engaging end of the second elongated member includes a partially or completely circumscribed opening, the illustrative embodiments described above with respect to the engaging end of the first elongated member may apply and will not be described in detail. In either configuration, the length or diameter of the partially or completely circumscribed opening of the engaging end of the second elongated member may be smaller than, equal to, or bigger than that of the partially or completely circumscribed opening of the engaging end of the first elongated member.

In still another embodiment, the engaging end of the second elongated member includes a support configured to at least partially correspond to the at least partially circumscribed opening of the engaging end of the first elongated member. Illustrative shapes of the support can include, but are not limited to, an ellipse, a circle, a square, a triangle with round corner contour, or partial configurations thereof. Partial configurations for supports may include any irregular shape to fit a particular site or purpose such as irregular formations in skin, tissue, muscle, and the like. For example, a partial configuration may include any of the above examples of shapes (ellipse, circle, square, triangle) having one or more indented portions or one or more protrusions. By providing partial configurations, additional flexibility is provided in the manner and type of locations in which the surgical instrument can be used. For example, a partial configuration may provide more access to an area than a regular, standard shaped support. Or, a partial configuration may provide a different ability to access an object being held by the surgical instrument. The length or diameter of the support can be in the range of about 1 cm to about 50 cm, about 2 cm to about 40 cm, about 3 cm to about 30 cm, about 5 cm to about 15 cm, about 1 cm to about 10 cm, about 1 cm to about 6 cm, or about 2 cm to about 5 cm, e.g. approximately 2 cm, 3 cm, 4 cm, 5 cm, 6 cm, 10 cm, or 15 cm, as illustrative examples, and may be smaller than, equal to, or bigger than the length or diameter of the partially or completely circumscribed opening of the engaging end of the first elongated member. As described above with respect to the engaging end of the first elongated member, the size of the support may depend on where and/or how the surgical instrument will be used.

The support can be a solid plate, mesh-like, or in other suitable configuration so long as support can be provided to an object (e.g. tissues, where it may be called a tissue support) held between the engaging ends of the first and second elongated members. Alternatively or additionally, the support may have a substantially flat surface, have a concave surface, have a raised surface, have an elevated surface, have a convex surface, or have a surface with one or more protrusions. In some embodiments, the substantially flat surface, concave surface, raised surface, elevated surface, convex surface, or surface with one or more protrusions is oriented toward the partially or completely circumscribed opening of the engaging end of the first elongated member. In one illustrative embodiment, the support is convex toward the partially or completely circumscribed opening of the engaging end of the first elongated member. In an illustrative embodiment, a solid plate that has a substantially flat surface for the support could be used where it is desired to generally be able to view and access a tissue region. In contrast, in some other embodiments, it may be desirable to be able to drain tissue while inspecting the tissue, in which case a mesh-like support may be used. In another embodiment, a raised surface or protruding surface for the support may be used to distort and/or contort the object being inspected. This may assist in exposing areas of the object, such as opening wounds in a tissue section for better inspection, making tumors or foreign objects in the depths of tissues (e.g. after local anesthesia where edema may be significant) more accessible, and the like. That same might also be true for using a convex surface, elevated surface, and the like.

The elongated portions of the first and second elongated members can be angled and/or curved, horizontally and/or longitudinally, as desired along a length of the elongated members; alternatively, the elongated portions may be straight. Further description about horizontal and/or longitudinal angles and curvature, is provided below. The particular configuration of the elongated portions may depend on factors such as, but not limited to, the particular application of the surgical instrument (e.g. the subject, the location, and the object to be held), the user's preference, etc., and will be apparent to those skilled in the art in light of the present disclosure. The first and second elongated portions can have the same or different lengths and/or cross-sectional thicknesses. In one embodiment, the first and second elongated portions have a length of about 5 cm to about 50 cm, or about 10 cm to about 40 cm, or about 20 cm to about 30 cm, e.g. approximately 10 cm, 12 cm, 15 cm, 20 cm, 25 cm, 30 cm, as illustrative examples. The cross-sectional thickness of the elongated portions can be about 2 mm to 20 mm, or about 4 mm to about 10 mm, or about 5 mm to about 7 mm, e.g. approximately 2 mm, 3 mm, 4 mm, 5 mm, 7 mm, 10 mm, 15 mm, as illustrative examples.

An edge of the partially or completely circumscribed opening of the engaging end of the first elongated member and/or the second elongated member may have a gripping surface and/or padding. In some embodiments, the edge of the circumscribed opening of each engaging end includes a gripping surface oriented toward each other to increase grip on objects being held therebetween. In embodiments where the engaging end of the second elongated member includes a support, a surface of the support oriented toward the partially or completely circumscribed opening of the engaging end of the first elongated member could be partially (e.g. along the edge) or completely covered with a gripping surface. The gripping surface may help prevent the object from slipping when the engaging ends are at least partially engaged with each other. Illustrative embodiments of a gripping surface may include, but are not limited to, a patterned surface, a surface with intermeshing ridges, and a surface covered with a material that can provide suitable friction when brought into contact with objects. Illustrative embodiments of such a material may include, but are not limited to, silica gel, rubber, plastics, and cloth. In yet other embodiments, the engaging ends can alternatively or additionally include a padding on the surfaces oriented toward each other to protect the objects being held, such as mucous membrane, from undesirable injury. The padding may also serve as a gripping surface described above. Illustrative materials for the padding may include, but are not limited to, silica gel, rubber, plastics, and cloth. In embodiments where an engaging end of the second elongated member includes a support, the padding may cover the whole or part (e.g. along the edge) of the surface of the support.

The handle ends of the first and second elongated members can include one or more of finger rings, gripping surfaces or transverse ridges. The handle ends may be in any suitable size and form to enable a user or technician to hold the surgical instrument. In some embodiments, the handle ends may be padded to enhance and/or comfort grip and the illustrative materials for padding as listed above with respect to the engaging ends may apply. The surgical instrument may also include a fastener at or near the handle for fixing the relative position of the first and second elongated members, including, but not limited to, a ratchet assembly, a screw type assembly, a snap fastener assembly, a gear assembly, and a clasp assembly, among others. Alternatively or additionally, a fastener may be provided elsewhere along the elongated member(s). In one embodiment, a fastener for fixing the relative position of the elongated members may be located further down along one or both elongated members. In another embodiment, a fastener is located between the connector and the handle ends. In yet another embodiment, a fastener is located between the engaging ends and the connector. In still another embodiment, the fastener can be located on the engaging ends themselves. While some illustrative embodiments will be described in more detail below, fasteners that may be used in the present instruments are well known to those skilled in the art and can be found in various medical instruments, such as, but not limited to, scissors and haemostats.

The surgical instrument may comprise one or more materials. In certain embodiments, one or more components of the surgical instrument may be manufactured from stainless steel, other metal and metal alloy, plastics, resin, medical ceramics, other suitable materials, or any combination thereof. In certain embodiments, at least part of the first elongated member, the second elongated member, the connector, and the fastener is made of stainless steel, other metal or metal alloy. In an illustrative embodiment, the engaging ends are made of plastics, and the handle ends are made of aluminum alloy. In another illustrative embodiment, the first elongated member, the second elongated member and the connector are made of stainless steel, and covered with plastics at the parts contacting the objects to be held (e.g., the engaging ends and surrounding areas). In some embodiments, the surgical instrument is disposable or reusable. Alternatively or additionally, the surgical instrument may be sterilizable.

Illustrative embodiments also include methods of operating a surgical instrument including operating a handle of a surgical instrument to place a partially or completely circumscribed opening of an engaging end of a first elongated member and a corresponding partially/completely circumscribed opening or a support of an engaging end of a second elongated member in an open or unengaged state. Methods may further include placing the partially or completely circumscribed opening of the engaging end of the first elongated member to at least partially frame a section of the treatment site. Methods may further include operating the handle of the surgical instrument to rotate the engaging ends relative to each other to place the engaging ends in a closed or engaged state, depending on whether an object is held therebetween. These and other embodiments will now be described in further detail with respect to the drawings.

In one aspect, the present disclosure provides a surgical instrument. FIG. 1 shows a perspective view of part of an illustrative embodiment of a surgical instrument 100. The surgical instrument 100 provided in the present disclosure includes a first elongated member 110 and a second elongated member 120. Each elongated member 110, 120 includes an engaging end 102a, 102b and an opposing handle end 104a, 104b, connected by an elongated portion 106a, 106b, respectively. The first elongated member 110 and the second elongated member 120 are interconnected through a connector 130 located between the engaging ends 102a, 102b and the handle ends 104a, 104b, and are configured to pivot around the connector 130. Thus, the connector 130 forms a pivot axis around which the first and second elongated members 110, 120, respectively, are pivotably connected.

The connector 130 may be located anywhere along the elongated portions 106a, 106b of the elongated members 110, 120, and may be any suitable connecting mechanism to allow the first elongated member 110 and the second elongated member 120 to pivot in relation to each other. In one embodiment, the pivot axis formed by the connector 130 provides that both the elongated members 110, 120 can pivot around the connector 130. In one embodiment, the elongated members 110, 120 can rotate such that an angle φ is about 0° to about 180°, about 2° to about 160°, about 5° to about 140°, about 10° to about 120°, or about 30° to about 90°, as illustrative examples. Although not shown, in one embodiment, a stop may be formed on one or both elongated members 110, 120 to limit the angle of rotation that one or both elongated members 110, 120 can pivot. Such a stop may be well known and used in the art.

The connector 130 may include simply an axis passing through holes in the first elongated member 110 and the second elongated member 120, or may include more complicated structures. In an illustrative embodiment, the connector 130 is a simple screw joint. In another illustrative embodiment, the connector 130 is a box joint which may prevent any shearing between the first and second elongated members 110, 120. In a further illustrative embodiment, the connector 130 may include a stub protruded from the elongated portion 106a or 106b of either the first or second elongated member 110 or 120 and inserted into a hole in the other one of the elongated portions 106a or 106b of the corresponding other elongated member 110 or 120. In still another illustrative embodiment, the connector 130 may include a rivet inserted into holes formed in both the elongated portions 106a and 106b. Other embodiments of connector 130 may be apparent to those skilled in the art.

In the embodiment of FIG. 1, the engaging end 102a of the first elongated member 110 includes a completely circumscribed opening 112, and the engaging end 102b of the second elongated member 120 includes a support 122 configured to correspond to circumscribed opening 112 of the engaging end 102a of the first elongated member 110. However, FIG. 1 is only an illustrative example of constructing the engaging ends 102a, 102b and some other alternatives are described further below and various other configurations will be understood by those of skill in the art based on the present disclosure.

The engaging end 102a of the first elongated member 110 and the engaging end 102b of the second elongated member 120 operate in conjunction to provide a working end 102. The handle end 104a of the first elongated member 110 and the handle end 104b of the second elongated member 120 operate in conjunction to provide a handle 104. As described below, a technician manipulates handle 104 which, due to the pivotable connection in the first and second elongated members 110, 120, operates to move the working end 102 between an open or unengaged state and a closed or engaged state. The engaging ends 102a, 102b are configured to operably engage with each other to hold an object.

In certain embodiments, one or more of the engaging ends 102a, 102b may be formed integrally with or be removably attached by any suitable mechanisms, such as, but not limited to, screws, clasps, pins, through holes, clips, nuts, bolts, adhesives, fasteners, or other mechanisms alone or in combination, to the elongated portions 106a, 106b of one or more of the elongated members 110, 120. A single surgical instrument with a set of engaging ends 102a, 102b with different sizes and shapes that can be removably attached to the surgical instrument may form a kit. Alternatively, a set of the surgical instruments with engaging ends 102a, 102b having different sizes and shapes may form a kit. In another embodiment, a set of the surgical instruments with engaging ends 102a, 102b and handle ends 104a, 104b having different sizes and shapes may form a kit. Other kit formats may be apparent to those skilled in the art in light of the present disclosure.

The completely circumscribed opening 112 in a shape of an ellipse as shown in FIG. 1 is one example of the engaging end 102a of the first elongated member 110. The circumscribed opening 112 may also be a partially circumscribed opening and may be in any other suitable shape and size adapted to the area subject to a surgical operation and/or an object to be held.

The support 122 in a shape of an ellipse and in a form of a solid plate having a slightly convex surface oriented toward the circumscribed opening 112 as shown in FIG. 1 is one example of the engaging end 102b of the second elongated member 120. The support 122 may be in any other configuration so long as it can provide support to objects (e.g. tissues) held between the engaging end 102a and the engaging end 102b when the engaging ends 102a, 102b are at least partially engaged with each other. For example, the support 122 may also be mesh-like. Alternatively or additionally, the support 122 may include a substantially flat surface 124, or the support 122 may include a concave surface 124 or a raised surface 124. In some embodiments, the substantially flat surface 124 is the surface oriented toward the circumscribed opening 112. In some embodiments, the concave surface 124 or the raised surface 124 is the surface oriented toward the circumscribed opening 112. Illustrative examples of a raised surface 124 may include, but are not limited to, a convex surface, an elevated surface, and a surface having one or more protrusions. The support 122 may be in any suitable shape and size adapted to the area subject to a surgical operation and/or an object to be held.

Furthermore, as detailed below, the engaging end 102b may also include a partially or completely circumscribed opening configured to at least partially correspond to the at least partially circumscribed opening of the engaging end 102a of the first elongated member 110. While in FIG. 1 the engaging end 102a is shown to include a circumscribed opening 112, and the engaging end 102b is shown to include a support 122, it will also be appreciated that both the engaging end 102a and engaging end 102b can have the same configuration. In one illustrative embodiment, both engaging ends 102a, 102b may include a circumscribed opening having the same or different shape and size. It may also be contemplated that both engaging ends 102a, 102b may include a support. In one illustrative embodiment, both supports are in the form of a solid plate having the same size or different sizes. In another illustrative embodiment, at least one support is mesh-like. In yet another illustrative embodiment, at least one support includes a concave surface oriented toward the other one.

In general, the contour of the engaging end 102b at least partially corresponds to the contour of the engaging end 102a. As shown in FIG. 1, the support 122 is configured to correspond to the shape and size of the circumscribed opening 112. However, it will be understood by those skilled in the art that the support 122 and the circumscribed opening 112 may be in the same shape or in different shapes, and the dimension of the support 122 may be larger than, equal to, or smaller than that of the circumscribed opening 112. The same applies to embodiments where the engaging end 102a of the first elongated member 110 includes a partially circumscribed opening and where the engaging ends 102b of the second elongated member 120 includes a partially or completely circumscribed opening. Illustrative shapes and dimensions of engaging ends 102a and 102b are discussed above.

In some embodiments, when the engaging end 102a and the engaging end 102b are in a closed state, the support 122 can be placed within the circumscribed opening 112 of the engaging end 102a. In certain embodiments, when the engaging end 102a and the engaging end 102b are in a closed state, the support 122 protrudes into or through the circumscribed opening 112 of the engaging end 102a.

Figure 2:
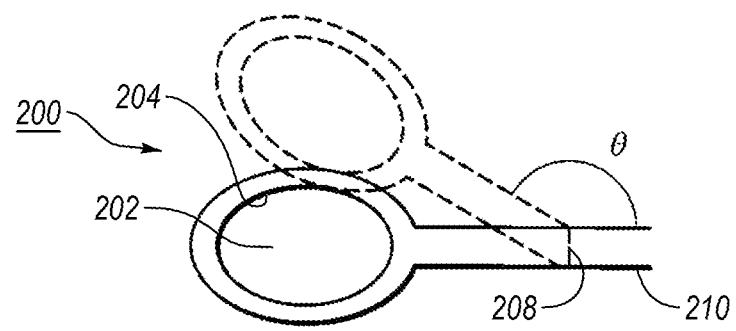
FIG. 2 shows a top view of a circumscribed opening of an illustrative embodiment of a surgical instrument.
Figure 3A:
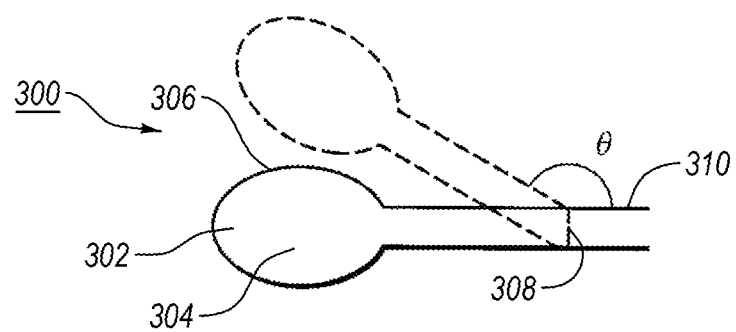
FIG. 3A and FIG. 3B show a top view and a side view of a support corresponding to the circumscribed opening of FIG. 2.
Figure 3B:
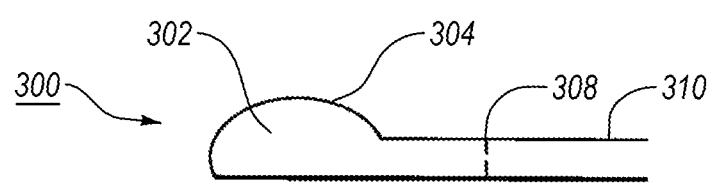

FIGS. 2 and 3A show a top view of an illustrative embodiment of the engaging end 200 of the first elongated member including a circumscribed opening 202 and the engaging end 300 of the second elongated member including a corresponding support 302 of a surgical instrument provide in the present disclosure. In this illustrative embodiment, both the circumscribed opening 202 and the support 302 are in the shape of an ellipse, and the support 302 matches the circumscribed opening 202 in size. FIGS. 2 and 3A also show that engaging end 200 and engaging end 300 can be horizontally angled with respect to the elongated portions 210, 310 at an angle point 208, 308 at an angle θ. Alternatively or additionally, the engaging end 200 and/or the engaging end 300 may be longitudinally angled (see e.g. FIG. 11 below). The angling points 208, 308 may be anywhere along the elongated portions 210, 310. In an illustrative embodiment, the angling point is at the connector (see e.g. FIG. 11 below). In another illustrative embodiment, the angling point is located between the engaging end and the connector. In yet another illustrative embodiment, the angling point is located between the connector and the handle end. Angling the engaging end 200 and engaging end 300 can assist a technician to be able to access difficult-to-reach treatment sites. Illustratively, angle θ can be approximately 90° to approximately 180°, or approximately 100° to approximately 170° or approximately 120° to approximately 160°, e.g. approximately 90°, 100°, 120°, 140°, 160°, or 170°. In some embodiments, angle θ could also be less than 90°. FIG. 3B shows a side view of the engaging end 300 showing that the support 302 can include a slightly convex surface 304 oriented toward the circumscribed opening 202. When the circumscribed opening 202 and the support 302 are in a closed state, an edge 204 of the circumscribed opening 202 and an edge 306 of the support 302 can be in full contact, and the slightly convex surface 304 of the support 302 can be within the circumscribed opening 202. In some other embodiments, circumscribed opening 202 and support 302 can be sized so edge 204 and edge 306 do not contact (see e.g. FIG. 4B below). In certain embodiments, the support 302 can even protrude into or through the circumscribed opening 202 (see e.g. FIG. 5 below).

Figure 4A:
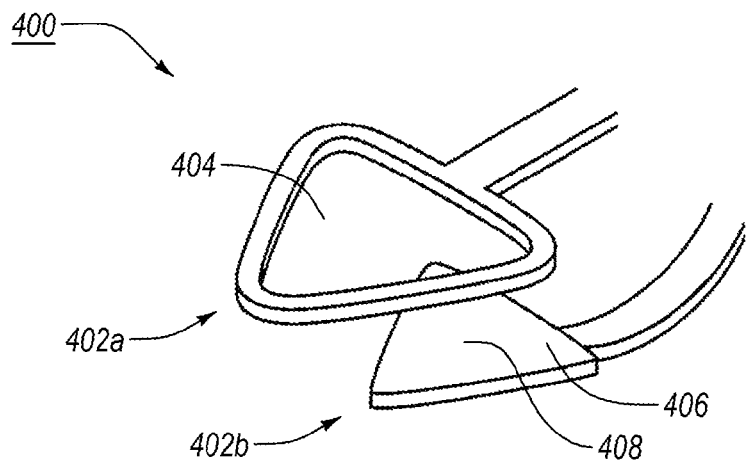
FIG. 4A and FIG. 4B show a perspective view and a top view of another illustrative embodiment of a surgical instrument.
Figure 4B:
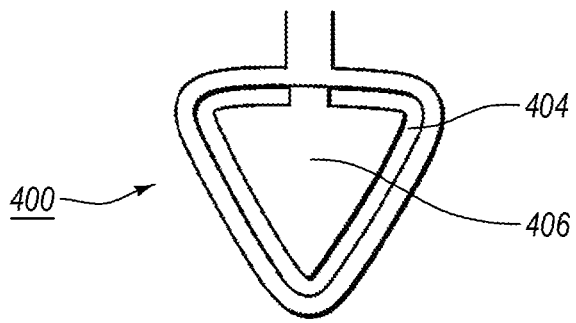

FIGS. 4A and 4B show a perspective view and a top view of another illustrative embodiment of the working end 400 including the engaging end 402a and the corresponding engaging end 402b of a surgical instrument provided in the present disclosure. In this illustrative embodiment, both the circumscribed opening 404 and the support 406 are in the shape of a triangle with round corner contour, and the support 406 is smaller than the circumscribed opening 404. The support 406 includes a substantially flat surface 408 oriented toward the circumscribed opening 404.

Figure 5:
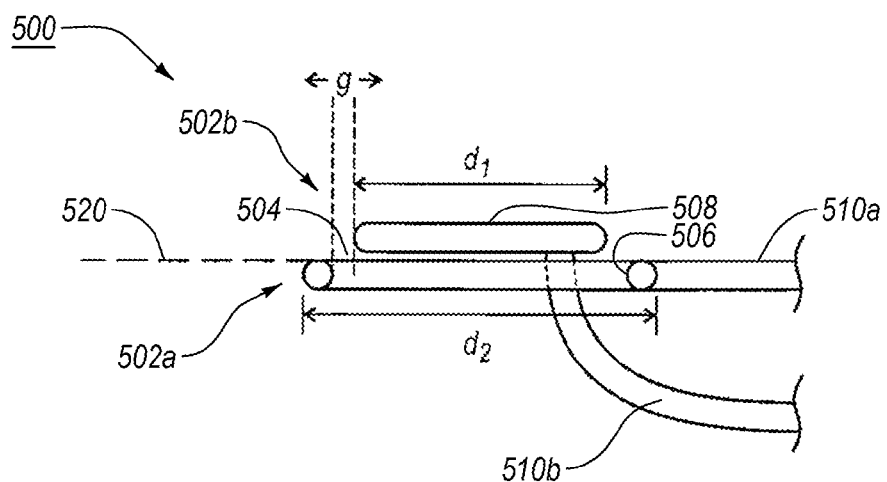
FIG. 5 shows a side view of an illustrative embodiment that could apply to embodiments shown in FIGS. 1, 2, 3A, 3B, 4A and 4B.

FIG. 5 shows a side view of an illustrative embodiment of the working end 500 that can apply to any of the embodiments shown in FIG. 1, 2, 3A, 3B, 4A or 4B. When the engaging end 502a of the first elongated member 510a and the engaging end 502b of the second elongated member 510b are in a closed state, the support 508 passes through the circumscribed opening 504 and passes beyond a plane 520 of the circumscribed opening 504, as shown in FIG. 5. In this embodiment, the diameter $d_1$ of the support 508 is less than a diameter $d_2$ of circumscribed opening 504 as defined by the edge 506, leaving a gap g between the circumscribed opening 504 and support 508.

Figure 6A:
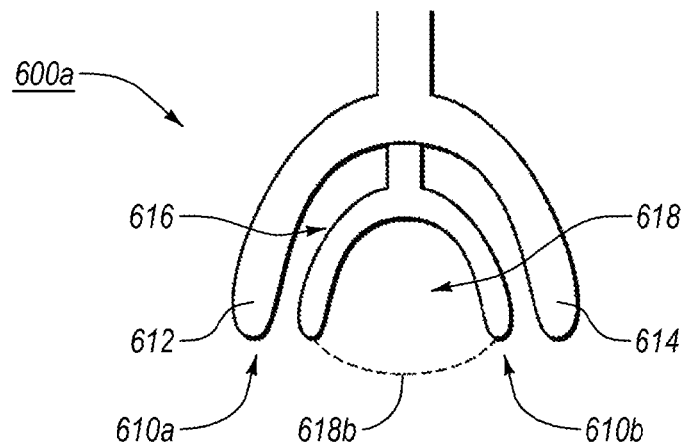
FIG. 6A shows a top view of an illustrative embodiment of a working end of a surgical instrument.
Figure 6B:
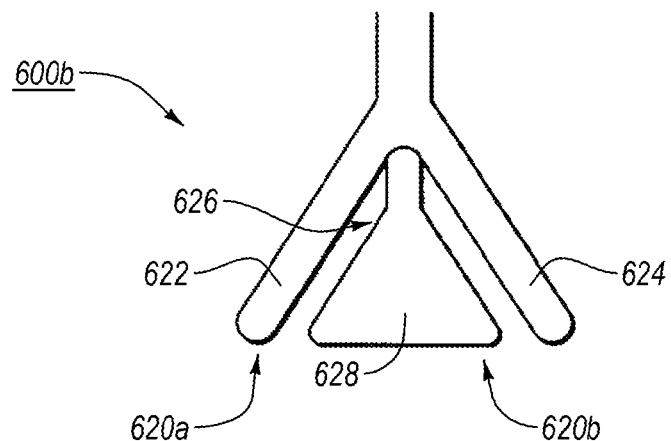
FIG. 6B shows a top view of another illustrative embodiment of a working end of a surgical instrument.

Turning to FIGS. 6A through 6B, other embodiments of working ends 600a, 600b are shown. In these embodiments, engaging ends 610a, 620a may not have a completely enclosed or circumscribed opening; rather embodiments are contemplated in which the engaging ends 610a, 620a include a partially circumscribed openings 616, 626 where, in contrast to a completely circumscribed opening, rims 612 and 614, 622 and 624 do not meet, forming a gap therebetween. As discussed above, a partially circumscribed opening may provide more access to an area near the gap than a completely circumscribed opening. Alternatively or additionally, a partially circumscribed opening may provide a different ability to engage an object being held by the surgical instrument. As mentioned above, the partially circumscribed opening may be configured in any suitable shape and size adapted to the area subject to a surgical operation and/or the object to be held. Illustrative shapes of the partially circumscribed opening may include, but are not limited to, a partial ellipse, partial circle, partial square, partial triangle, an irregular shape, or other shape. This may result in embodiments of the engaging ends 610a, 620a having a "C" shape (FIG. 6A), or "V" shape (FIG. 6B) which are provided as illustrative examples. While these standard shapes are provided as examples, the partially circumscribed opening can also be an irregular shape to fit a particular site or purpose such as irregular formations in skin, tissue, muscle, and the like. Other configurations of shape and/or curvature are possible for engaging ends 610a, 620a in light of the disclosure herein.

FIGS. 6A and 6B also show some illustrative embodiments of engaging ends 610b, 620b. The engaging ends 610b, 620b are configured to at least partially correspond to the engaging ends 610a, 620a. In one illustrative embodiment, engaging end 610b may also include a partially circumscribed opening 618 of the same shape/contour as the partially circumscribed opening 616 of the engaging end 610a, as shown in FIG. 6A. A dashed line indicates that engaging end 610b may also include a completely circumscribed opening 618b. In another illustrative embodiment, as shown in 6B, the engaging end 620b includes a support 628 formed from a triangle-shaped solid plate. As shown in FIGS. 6A and 6B, the engaging ends 610b, 620b may be sized to be smaller than the engaging ends 610a, 620a so that engaging ends 610b, 620b are placed within or even protrude into or through the partially circumscribed openings 616, 626 when the working ends 600a, 600b are in a closed state, and the illustrative embodiment shown in FIG. 5 may also apply here. However, as mentioned above, the engaging ends 610b, 620b may also be larger than, or equal to the engaging ends 610a, 620a.

FIGS. 7 through 10 show illustrative embodiments of the handle of the surgical instrument provided in the present disclosure. The handle end of the first elongated member and the handle end of the second elongated member may act in conjunction to provide a handle. The handle ends may be in any suitable size and form to enable a user or technician to hold the surgical instrument. In some embodiments, one or more of the handle ends may include a finger ring. In some embodiments, one or more of the handle ends may be elongated and include a gripping surface and/or transverse ridges. In some embodiments, one of the handle ends may include a finger ring, while the other one of the handle ends may be elongated and include a gripping surface and/or transverse ridges.

Figure 7:
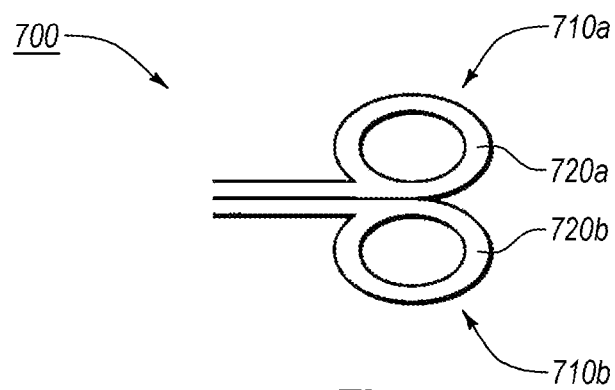
FIG. 7 through FIG. 10 show illustrative embodiments of a handle of a surgical instrument.

FIG. 7 shows an illustrative embodiment of a handle 700 formed by the handle ends 710a, 710b. In this illustrative embodiment, both handle ends 710a, 710b include a finger ring 720a, 720b, respectively, like those for scissors.

Figure 8:
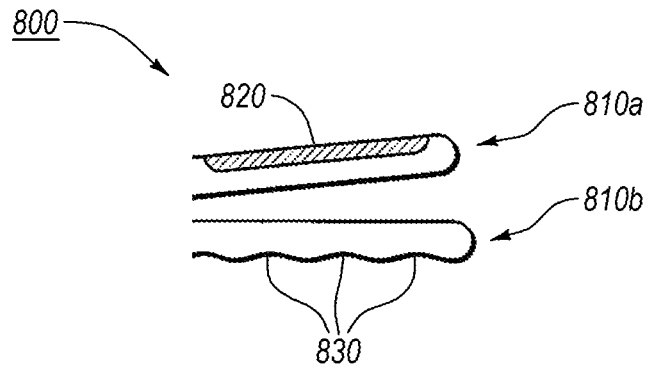

FIG. 8 shows another illustrative embodiment of a handle 800 formed by the handle ends 810a, 810b. In this illustrative embodiment, the handle end 810a includes a patterned gripping surface 820 facing toward a palm of a user or technician, whereas the handle end 810b includes a number of depressions 830 on the opposite side that fit the fingers of the user or technician operating the surgical instrument.

The surgical instrument provided in the present disclosure may further include a fastener for fixing the relative position of the elongated members. As discussed above, the fastener may be located on the handle ends themselves, on the elongated portions associated with the handle ends, and/or elsewhere along the elongated members. Illustrative embodiments of the fastener may include, but are not limited to, a ratchet assembly, a screw type assembly, a snap fastener assembly, a gear assembly, and a clasp assembly. In certain embodiments, the fastener may be an assembly that can fix the relative position of the elongated members, in particular the engaging ends during operation, and when opposite forces are applied, release the two elongated members from fixation. In an illustrative embodiment, the fastener 158 may be semi-arcwise. In another illustrative embodiment, the fastener may be equidistant-gear-shaped. In yet another illustrative embodiment, a simple ratchet assembly can be applied which includes both the handle ends having interlocking teeth that can be released and secured to lock the handle ends together, such as that used in a hemostat.

Figure 9:
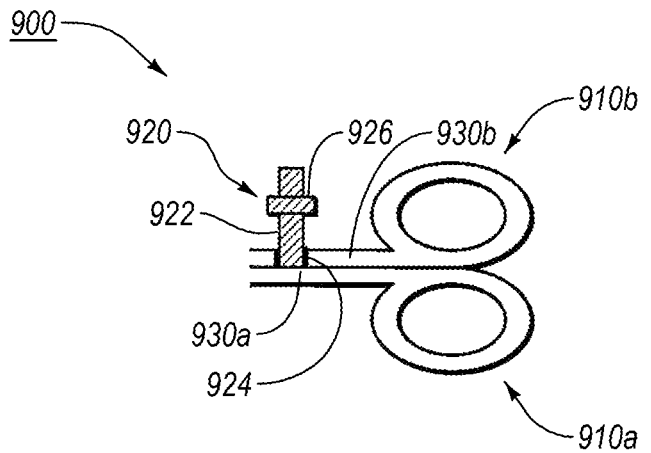

FIG. 9 shows an illustrative embodiment of a handle 900 formed by the handle ends 910a, 910b with a screw-type fastener 920, in which a screw bolt 922 is provided on the first elongated member 930a and passed through a bore 924 provided on the second elongated member 930b. Alternatively, the screw bolt 922 may be provided on the second elongated member 930b and the bore 924 may be provided on the first elongated member 930a. A screw nut 926 rotates on the screw bolt 922 to contact the second elongated member 930b or the first elongated member 930a to confine the relative movement of the handle ends 910a, 910b of the surgical instrument. Such an assembly may also function as a stop as mentioned above.

Figure 10:
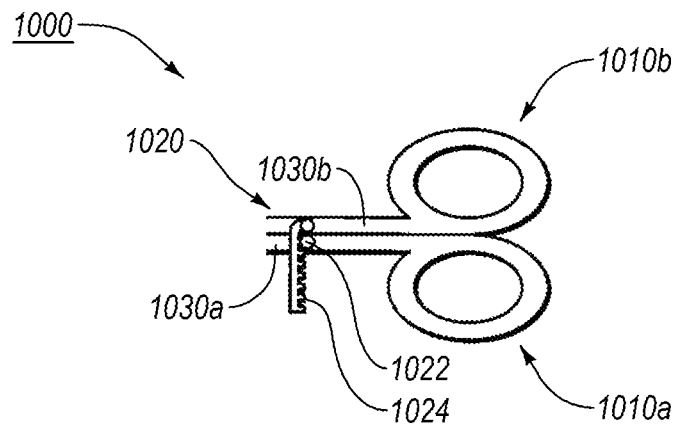

FIG. 10 shows another illustrative embodiment of a handle 1000 formed by the handle ends 1010a, 1010b with a snap fastener assembly 1020, in which a small bar 1022 provided on the first elongated member 1030a can be snapped into different recesses in a fastener arm 1024 provided on the second elongated member 1030b so that the elongated members 1030a, 1030b can be fixed in different relative angular position. Alternatively, the small bar 1022 may be provided on the second elongated member 1030b and the fastener arm 1024 may be provided on the first elongated member 1030a.

Figure 11:
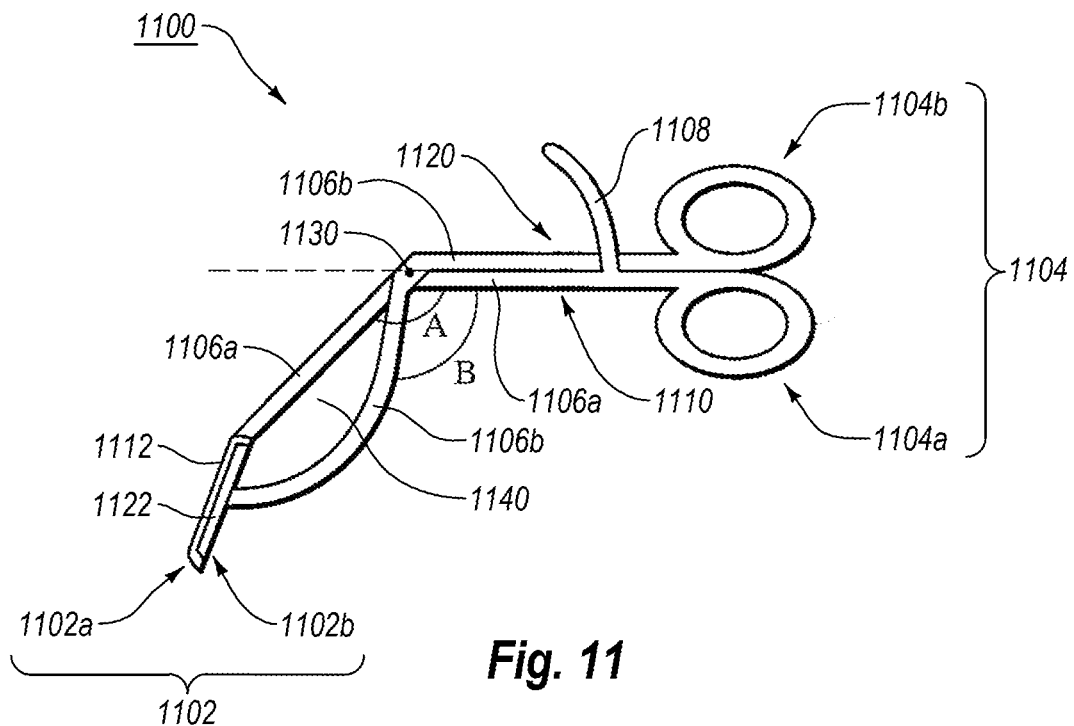
FIG. 11 shows a side view of an illustrative embodiment of a surgical instrument.

FIG. 11 is a side view of an illustrative embodiment of the surgical instrument 1100. As shown in FIG. 11, the surgical instrument 1100 includes: a first elongated member 1110; a second elongated member 1120; and a connector 1130 interconnecting the first elongated member 1110 and the second elongated member 1120 such that the first elongated member 1110 and the second elongated member 1120 pivot around the connector 1130. The connector 1130 is located on the elongated portions 1106a, 1106b of the first elongated member 1110 and the second elongated member 1120 between the engaging end 1102a, 1102b and the handle end 1104a, 1104b, and is positioned in an intermediate location of the first elongated member 1110 and the second elongated member 1120, but is not necessary to be at the center of the first elongated member 1110 or the second elongated member 1120.

Each of the first elongated member 1110 and the second elongated member 1120 includes an engaging end 1102a, 1102b and a handle end 1104a, 1104b, connected by an elongated portion 1106a, 1106b, respectively. As shown in FIG. 11, the surgical instrument 1100 further includes a fastener 1108 for fixing the relative position of the first elongated member 1110 and the second elongated member 1120. The engaging end 1102a of the first elongated member 1110 includes a circumscribed opening 1112, and the engaging end 1102b of the second elongated member 1120 includes a support 1122 configured to correspond to the circumscribed opening 1112. The engaging ends 1102a, 1102b cooperate to form a working end 1102. A technician may manipulate the handle 1104, and, due to the pivotable connection formed by the connector 1130 in the first elongated member 1110 and second elongated member 1120, moves the working end 1102 from an unengaged state to an engaged state to hold an object between the engaging end 1102a and the engaging end 1102b, e.g. to confine a region for surgical treatment. In some embodiments, the firmness with which the engaging ends 1102a, 1102b hold an object is sufficient to achieve compression hemostasis in the surrounding tissue, as with a hemostat, which may facilitate operation on the region.

In certain embodiments, at least a portion of the elongated portion 1106a connecting the engaging end 1102a and the handle end 1104a of the first elongated member 1110 and/or the elongated portion 1106b connecting the engaging end 1102b and the handle end 1104b of the second elongated member 1120 may be curved and/or bent such that when the engaging end 1102a and the engaging end 1102b come in close proximity with each other, e.g. in a closed or engaged state, there is a gap 1140 between the at least a portion of the elongated portion 1106a of the first elongated member 1110 and the elongated portion 1106b of the second elongated member 1120. By creating such a gap 1140, additional tissues and/or other objects may be held there. This may allow access to deeper location and/or otherwise facilitate surgical procedures. In an illustrative embodiment, as shown in FIG. 11, the elongated portion 1106a of the first elongated member 1110 between the engaging end 1102a and the connector 1130 is straight, and the elongated portion 1106b of the second elongated member 1120 between the engaging end 1102b and the connector 1130 is curved (see also FIG. 1). In another illustrative embodiment, the elongated portion 1106a of the first elongated member 1110 between the engaging end 1102a and the connector 1130 is curved, and the elongated portion 1106b of the second elongated member 1120 between the engaging end 1102b and the connector 1130 is straight. In yet another illustrative embodiment, both the elongated portion 1106a of the first elongated member 1110 between the engaging end 1102a and the connector 1130 and the elongated portion 1106b of the second elongated member 1120 between the engaging end 1102b and the connector 1130 are curved such that the gap 1140 may be in a shape of a circle or ellipse or the like when the engaging ends 1102a, 1102b are at least partially engaged with each other or in a closed state. In some embodiments, the gap 1140 does not need to encompass the entire distance between the engaging ends 1102a, 1102b and the connector 1130, and may be formed adjacent to the engaging ends 1102a, 1102b or to the connector 1130. Alternatively or additionally, a gap may be formed between the connector 1130 and the handle ends 1104a, 1104b.

As shown in FIG. 11, the elongated portions 1106a, 1106b are longitudinally angled and form an angle A and an angle B, respectively. While the angles A, B are shown being formed at the connector 1130, the angling points do not necessarily need to be formed near the connector 130; rather the angles A, B may be formed elsewhere along the elongated portions 1106a, 1106b. In some embodiments, angles A and B are of the same degree. In some other embodiments, angles A and B are of different degrees, e.g. when at least a portion of elongated portions 1106a and/or elongated portion 1106b is curved or bent and a gap 1140 is present therebetween, as shown in FIG. 11. The angles A, B may be in a range of approximately 90° to approximately 180°, or approximately 100° to approximately 170° or approximately 120° to approximately 160°, e.g. approximately 90°, 100°, 120°, 140°, 160°, or 170°. In some embodiments, the angles A, B could also be less than 90°. In certain embodiments, the elongated portions 1106a, 1106b are in the same plane. In certain embodiments, the elongated portions 1106a, 1106b are not located in one plane along their entire lengths. In one illustrative embodiment, the elongated portions 1106a, 1106b may be both horizontally and longitudinally angled so that the section of the elongated portions on one side of the angling point is in a different plane than the section of the elongated portions on the other side of the angling point. In another illustrative embodiment, likewise, the elongated portions 1106a, 1106b may be both horizontally and longitudinally curved. In yet another illustrative embodiment, one of the elongated portions is horizontally curved and the other is longitudinally curved. Other embodiments will be apparent to those skilled in the art in light of the present disclosure.

In certain embodiments, the surgical instrument provided in the present disclosure may be used in oral surgeries, for example, to remove tumors in a genal region. The surgical instrument may also be used in other regions and for other objects, including, but not limited to, lymph nodes, hematoma, and foreign substances, such as steel balls and bullets. It should be understood, however, that the present surgical instrument may find use in various applications to facilitate surgical procedures, e.g. by confining a treatment site and/or achieving compression hemostasis.

Illustratively, the surgical instrument provided in the present disclosure may, for example, be operated in accordance with the following illustrative methods when it is adapted to treat tumors in genal region. But it should be understood that the present disclosure is in no way limited to the following embodiments.

Using the illustrative embodiment of FIG. 11 as an example, in one embodiment, an illustrative method includes operating a handle 1104 of a surgical instrument 1100 to place the engaging end 1102a and engaging end 1102b away from each other in an open state or an unengaged state. At least one of engaging end 1102a or 1102b of the instrument 1100 can be placed at a tumor site (properly constructing instrument 1100 based on the subject, the location and/or size of the tumor site, among other factors) such that a space enclosed by the circumscribed opening 1112 frames a section of the bucca. The handle 1104 can be operated to rotate the other of the engaging ends 1102a, 1102b relative to the engaging end 1102a or 1102b that was first placed at the site to place the working end 1102 in an engaged state. The instrument 1100 can be fastened by the fastener 1108 to fix the engaging end 1102a relative to the engaging end 1102b. In one embodiment, when the engaging end 1102a cooperates with the engaging end 1102b to tightly hold the soft tissue, the soft tissue will be fixed and the tumor within the soft tissue may even be pushed or extruded through the space defined by the circumscribed opening 1112 by the support 1122. With the tissue fixed, a surgeon can then operate to cut the tumor off of the tumor site and suture the incision. The method can include releasing the fastener 1108 to loosen the instrument 1100. If no obvious bleeding is observed, the handle 1104 can be operated to move the engaging end 1102a and engaging end 1102b away from each other. The whole instrument 1100 can then be removed from the mouth.

Figure 12:
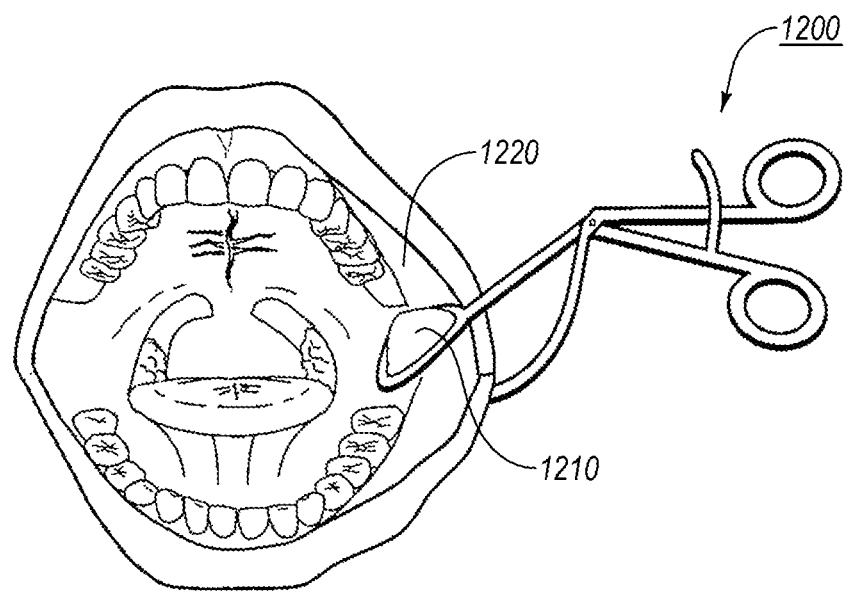
FIG. 12 is a schematic diagram showing an illustrative application in an oral surgery of an illustrative embodiment of a surgical instrument.

FIG. 12 shows the illustrative embodiment of using a surgical instrument 1200 to fix a tumor 1210 in a genal region 1220. As shown in FIG. 12, the tumor 1210 is fixed and raised by the surgical instrument 1200 so as to facilitate the operation on the tumor 1210.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

While certain embodiments have been illustrated and described, it should be understood that changes and modifications can be made therein in accordance with ordinary skill in the art without departing from the technology in its broader aspects as defined in the following claims. For example, while the orientation of the engaging end 14a and engaging end 14b of FIG. 1 have been described and shown to allow access to a surgical site in the buccal region, it will be appreciated that the configurations of the engaging end 14a and engaging end 14b could be reversed so that the engaging end 14a has a support and the engaging end 14b has a circumscribed portion to allow access to a tumor on the opposing side of the buccal region. Also, the surgical instruments disclosed herein could be configured for left-handed technicians as well as right-handed technicians.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A surgical instrument, comprising:
   a first elongated member and a second elongated member each comprising an engaging end and a handle end connected by an elongated portion; and
   a connector located between the engaging end and the handle end of each elongated member, the connector interconnecting the first elongated member and the second elongated member such that the first elongated member and the second elongated member are configured to pivot around the connector,
   wherein the engaging end of the first elongated member includes an at least partially circumscribed opening extending outward from the first elongated member in a plane transverse to a longitudinal axis thereof, and
   wherein the engaging end of the second elongated member includes a plate-shaped support extending outward from the second elongated member in a plane transverse to a longitudinal axis thereof, the plate-shaped support having a top surface, a bottom surface and a peripheral boundary extending therebetween, wherein one or more of the bottom surface and the top surface is integrally formed at the engaging end of the second elongated member, wherein the peripheral boundary is sized and configured to enable the bottom surface of the plate-shaped support to pass through a plane of a top surface of the at least partially circumscribed opening when the engaging ends are in a closed state, and wherein the peripheral boundary of the plate-shaped support is configured to fully correspond to the peripheral boundary of the at least partially circumscribed opening.

2. The surgical instrument according to claim 1, wherein the first elongated member and second elongated member are spaced apart from one another when the engaging ends are in the closed state.

3. The surgical instrument according to claim 1, wherein at least one of an edge of the at least partially circumscribed opening and the plate-shaped support further includes at least one of:
   a padding comprising at least one of silica gel, plastics, and cloth; or
   a gripping surface in the form of one or more of a patterned surface, a surface with intermeshing ridges, and a surface covered with a material selected from the group consisting of silica gel, rubber, plastic, cloth and any combination thereof.

4. The surgical instrument according to claim 1, wherein one or more of the elongated portions connecting the engaging ends and the handle ends are configured to form at least one of a horizontal angle and a longitudinal angle and the at least one of the horizontal angle and the longitudinal angle are in a range of approximately 90° to approximately 170°.

5. The surgical instrument according to claim 1, wherein the top surface of the plate-shaped support includes a substantially flat surface oriented toward the at least partially circumscribed opening.

6. The surgical instrument according to claim 1, wherein the plate-shaped support is a mesh-like material.

7. The surgical instrument according to claim 1, wherein the peripheral boundary of the plate-shaped support at least partially corresponds to a peripheral boundary of the at least partially circumscribed opening.

8. The surgical instrument according to claim 1, wherein the at least partially circumscribed opening is in the shape of a circle, an ellipse, a square, or a triangle with round corner contour.

9. The surgical instrument according to claim 1, wherein the first elongated member and the second elongated member are configured to pivot about the connector such that the bottom surface of the plate-shaped support of the second elongated member passes completely through and is positioned above the plane of the top surface of the at least partially circumscribed opening of the first elongated member in the closed state.

10. A surgical instrument, comprising:
   a first elongated member and a second elongated member, each comprising an engaging end and a handle end connected by an elongated portion; and
   a connector located between the engaging end and the handle end of each elongated member, the connector interconnecting the first elongated member and the second elongated member such that the first elongated member and the second elongated member are configured to pivot around the connector to move the engaging ends between an open state and a closed state,
   wherein the engaging end of the first elongated member includes a first circumscribed opening, and the engaging end of the second elongated member includes a second circumscribed opening integrally formed at the engaging end of the second elongated member and having a solid top surface and a solid bottom surface and a peripheral boundary extending therebetween, the peripheral boundary sized to fit within an interior boundary of the first circumscribed opening of the first elongated member such that the solid top and bottom surfaces of the second circumscribed opening of the second elongated member completely pass through a plane of a top surface of the first circumscribed opening of the first elongated member in the closed state.

11. The surgical instrument according to claim 10, wherein the second elongated member includes a curved region that defines a gap between the first and second elongated members in the closed state.

12. The surgical instrument according to claim 10, wherein the first and second circumscribed openings extend outwardly in opposite directions from the first and second elongated members in a plane substantially perpendicular to a plane of rotation around the connector.

13. The surgical instrument according to claim 10, wherein the first and second elongated members are spaced apart from one another in the closed state.

14. A surgical instrument, comprising:
   a first elongated member and a second elongated member each comprising an engaging end and a handle end connected by an elongated portion; and
   a connector located between the engaging end and the handle end of each elongated member, the connector interconnecting the first elongated member and the second elongated member such that the first elongated member and the second elongated member are configured to pivot around the connector,
   wherein the engaging end of the first elongated member includes an at least partially circumscribed opening extending outward from the first elongated member in a plane transverse to a longitudinal axis thereof, and
   wherein the engaging end of the second elongated member includes a plate-shaped support extending outward from the second elongated member in a plane transverse to a longitudinal axis thereof, the plate-shaped support having a top surface, a bottom surface and a peripheral boundary extending therebetween, wherein one or more of the bottom surface and the top surface is integrally formed at the engaging end of the second elongated member, wherein the peripheral boundary is sized and configured to enable the bottom surface of the plate-shaped support to pass through a plane of a top surface of the at least partially circumscribed opening when the engaging ends are in a closed state and wherein the plate-shaped support is a mesh-like material.

* * * * *